US00PP29005P2

(12) United States Plant Patent
Eveleens

(10) Patent No.: US PP29,005 P2
(45) Date of Patent: Feb. 27, 2018

(54) ***HYDRANGEA* PLANT NAMED 'HORTHAMP'**

(50) Latin Name: *Hydrangea macrophylla*
Varietal Denomination: Horthamp

(71) Applicants: Horteve Breeding BV, De Kwakel (NL); Kolster Holding BV, Boskoop (NL)

(72) Inventor: Cornelis Pieter Eveleens, De Kwakel (NL)

(73) Assignees: HORTEVE BREEDING B.V., Aalsmeer (NL), part interest; KOLSTER HOLDING B.V., Boskoop (NL), part interest ( * ) Notice: Subject to any disclaimer, the term of this patent is extended or adjusted under 35 U.S.C. 154(b) by 0 days.

(21) Appl. No.: 15/330,917

(22) Filed: Nov. 14, 2016

(51) Int. Cl.
*A01H 5/02* (2006.01)

(52) U.S. Cl.
USPC ..... Plt./250

(58) Field of Classification Search
USPC ..... Plt./250
See application file for complete search history.

*Primary Examiner* — Annette H Para
(74) *Attorney, Agent, or Firm* — Penny J. Aguirre

(57) ABSTRACT

A new cultivar of *Hydrangea macrophylla* plant named 'Horthamp' that is characterized by its picotee sterile flowers with sepals that are white in color with deep reddish pink margins when young and becoming pink in color with similar margins when mature and its sterile flower sepals with occasional green streaks.

2 Drawing Sheets

Botanical classification: *Hydrangea macrophylla.*
Varietal denomination: 'Horthamp'.

CROSS REFERENCE TO A RELATED APPLICATION

This application is co-pending with a U.S. Plant Patent Application filed for a plant derived from the same breeding program that is entitled *Hydrangea* Plant Named 'Hortfire' (U.S. Plant patent application Ser. No. 15/330,916).

BACKGROUND OF THE INVENTION

The present invention relates to a new and distinct cultivar of *Hydrangea macrophylla* and will be referred to hereafter by its cultivar name, 'Horthamp'. 'Horthamp' represents a new bigleaf *hydrangea*, a perennial shrub grown for landscape use.

'Horthamp' was derived from an ongoing controlled breeding program directed by the Inventor in Boskoop, The Netherlands. The objective of the breeding program was to develop new cultivars of *Hydrangea* with sterile flower sepals that are picotee with pink or red edges. 'Horthamp' arose from a controlled cross made by the Inventor in June of 2008 between unnamed and unpatented proprietary plants in the Inventor's breeding program; reference no. 07-036-01 as the female parent and reference no. 07-120-04 as the male parent. 'Horthamp' was initially selected a single unique plant from amongst the resulting seedlings for further evaluation in 2010 and characteristics confirmed in June of 2013.

Asexual propagation of the new cultivar was first accomplished by stem cuttings by the Inventor in Boskoop, The Netherlands in July of 2010. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Horthamp' as a unique cultivar of *Hydrangea macrophylla.*

1. 'Horthamp' exhibits picotee sterile flowers with sepals that are white in color with deep reddish pink margins when young and becoming pink in color with similar margins when mature.
2. 'Horthamp' exhibits sterile flower sepals with occasional green streaks.

The female parent of 'Horthamp' differs from 'Horthamp' in having a shorter plant height and in having sterile flower sepals that lack green markings. The male parent of 'Horthamp' differs from 'Horthamp' in having a taller plant size and in having sterile flower sepals that remain white with pink picotee margins as they mature. 'Horthamp' can be most closely compared to the *Hydrangea macrophylla* cultivars 'Hortmaclepa' (U.S. Plant Pat. No. 27,787), 'Hortmaflam' (U.S. Plant Pat. No. 27,716), and 'Hortfire'. These cultivars are similar to 'Horthamp' in having picotee sterile flowers. 'Hortmaclepa' differs from 'Horthamp' in having sterile flower sepals with narrower pink picotee margins, undulate margins, in lacking green markings, and in remaining white with pink picotee margins as they mature. 'Hortmaflam' differs from 'Horthamp' in having sterile flower sepals with serrated margins, that lack green markings, and that remain white with pink picotee margins s they mature. 'Horfire' differs from 'Horthamp' in having sterile flower sepals with wavy margins and in lacking green markings.

BRIEF DESCRIPTION OF THE DRAWINGS

The accompanying colored photographs illustrate the overall appearance and distinct characteristics of the new *Hydrangea*. The photographs were taken of a plant two years in age as grown in a 21-cm container in a greenhouse in Boskoop, The Netherlands.

The photograph in FIG. 1 provides a side view of the plant habit of 'Horthamp' in bloom.

Figure 1:
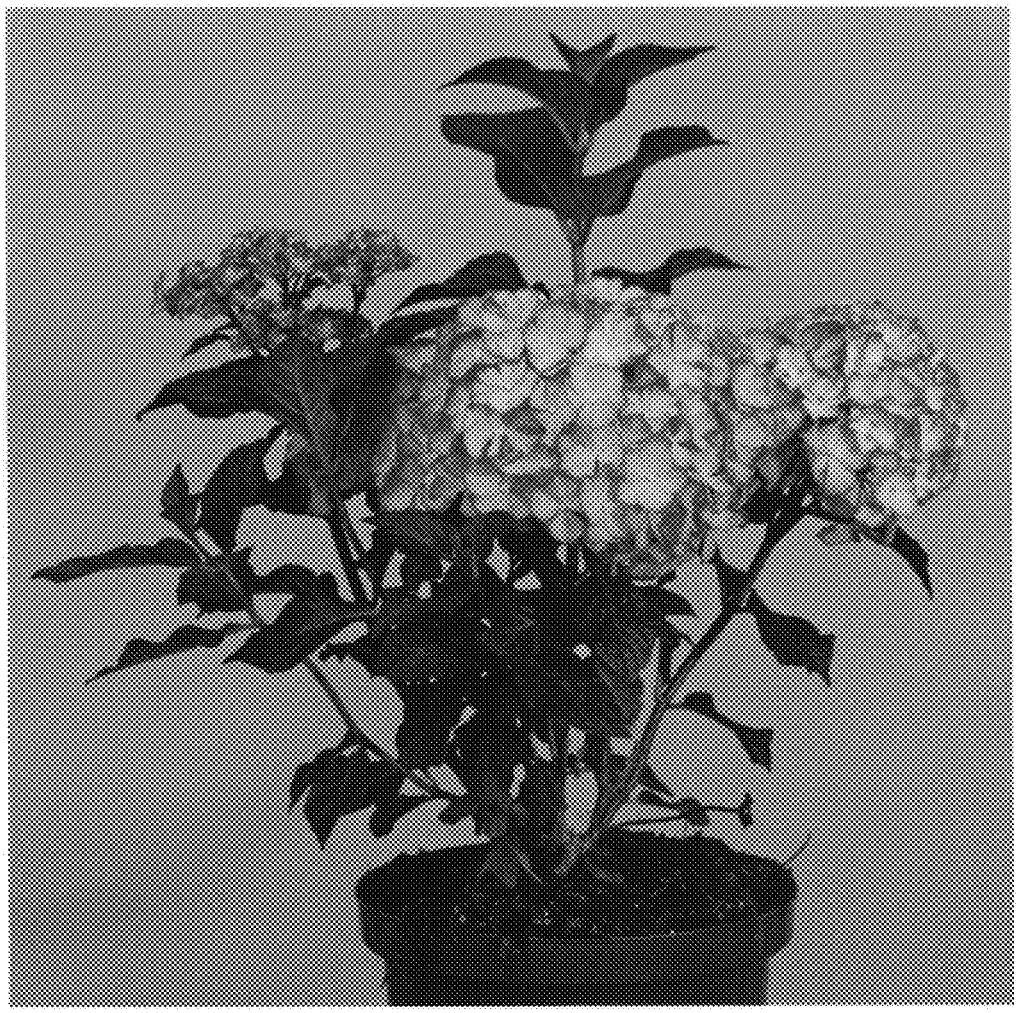
Figure 2:
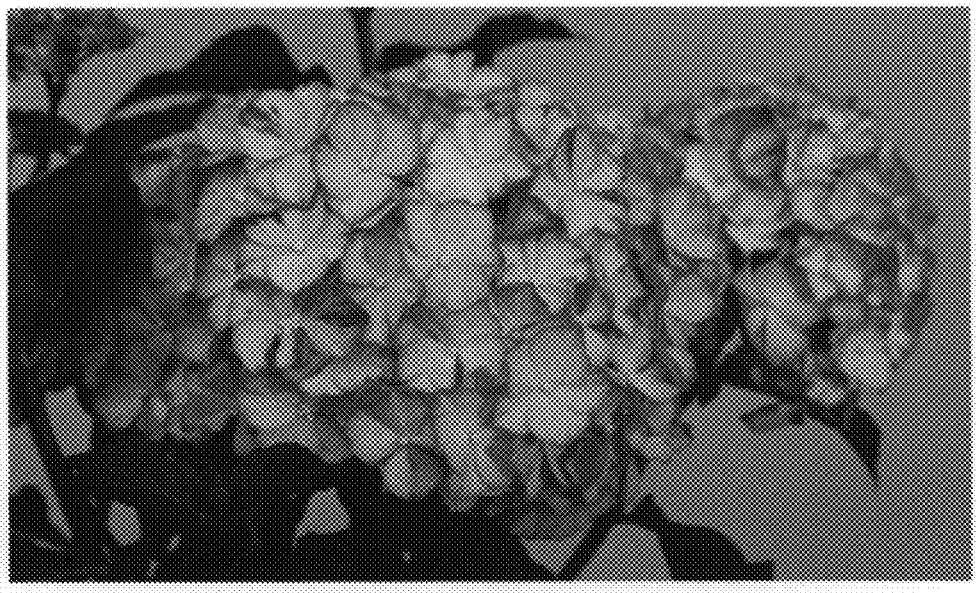

The photograph in FIG. 2 provides a close-up view of an inflorescence of maturing and mature inflorescences of 'Horthamp'.

Figure 3:
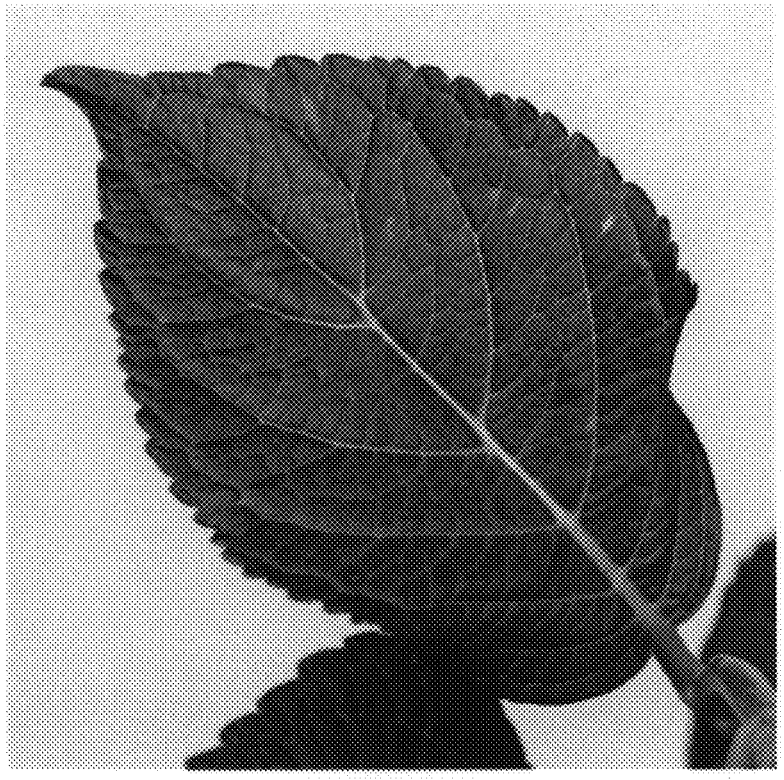

The photograph in FIG. 3 provides a close-up view of the lower surface of a leaf of 'Horthamp'.

The colors in the photographs are as close as possible with the photographic and printing technology utilized and the color values cited in the detailed botanical description accurately describe the colors of the new *Hydrangea.*

BOTANICAL DESCRIPTION OF THE PLANT

The following is a detailed description of plants two years in age as grown in 21-cm containers in a greenhouse in Boskoop, The Netherlands. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period.*—From May to July in a greenhouse and from July to September outside in The Netherlands.

*Plant type.*—Perennial shrub, mophead type *hydrangea.*

*Plant habit.*—Broadly spreading to upright.

*Height and spread.*—Up to 1.5 m in height and 2 m in spread after a few years in the landscape.

*Hardiness.*—At least in U.S.D.A. Zones 5 to 9.

*Diseases and pests.*—No susceptibility or resistance to pests and diseases has been observed.

*Root description.*—Fibrous and fine, 199D in color.

*Propagation.*—Stem cuttings.

*Time required for root development.*—An average of 3.5 weeks for root initiation with a young rooted plant produced in an average of six months.

*Growth rate.*—Moderate.

Stem description:

*Stem shape.*—Rounded.

*Stem strength.*—Strong.

*Stem aspect.*—Upright to an average angle of 55° to soil.

*Stem color.*—Immature stems; 144A, mature stems; 144A, older bark; N199A to N199C.

*Stem size.*—An average of 23.7 cm (excluding the inflorescence) in length and 6 mm in diameter.

*Stem surface.*—Immature and mature stems; glabrous and densely lenticellate with lenticels; an average of 1 mm in length and 0.5 mm in width, and N186C in color.

*Branching.*—Moderately branched with an average of 10 lateral branches, branching improves with pinching.

*Internode length.*—An average of 5 cm.

Foliage description:

*Leaf shape.*—Ovate to elliptic.

*Leaf arrangement.*—Opposite.

*Leaf division.*—Simple.

*Leaf number.*—An average of 6 (3 pairs) per lateral branch.

*Leaf base.*—Rounded to cuneate.

*Leaf apex.*—Apiculate.

*Leaf margins.*—Serrate.

*Leaf venation.*—Pinnate, color; upper surface 146B and lower surface 147B suffused with 200C to 200D at the margins, lower surface main and lateral veins are covered with short hairs; an average of 0.2 mm in length and 144D in color.

*Leaf size.*—An average of 11.4 cm in length and 7 cm in width.

*Leaf attachment.*—Petiolate.

*Leaf surface.*—Upper and lower surfaces; smooth and moderately rugose.

*Leaf color.*—Young leaves; upper surface 143A strongly suffused with 200A and lower surface 148B suffused with 200C at the margin and apex, mature leaves; upper surface a blend between NN137A and 147A and lower surface NN137A to NN137B suffused with 200A at the margins.

*Petioles.*—An average of 1.1 cm in length and 4 mm in diameter, color; upper surface 144B and lower surface 144A, both surfaces; smooth and moderately glossy surface, strong.

Inflorescence description:

*Inflorescence type.*—Flattened globular, mophead type, compound corymb of rotate-shaped sterile flowers.

*Lastingness of inflorescence.*—Sterile flowers; an average of 6 weeks, sepals persistent, petals self-cleaning, fertile flowers; an average of 1 week, self-cleaning.

*Inflorescence number.*—One per lateral stem.

*Inflorescence size.*—An average of 11.5 cm in height and 16.3 cm in diameter.

*Flower number.*—An average of 185 sterile flowers and 80 fertile flowers per inflorescence.

*Flower fragrance.*—None.

*Flower aspect.*—Sterile flowers; upright, outwards, and slightly drooping, fertile flowers; upright.

*Flower size.*—Sterile flowers; an average of 4.2 cm in diameter and 1.3 cm in depth, fertile flowers; an average of 5 mm in diameter and 4 mm in depth.

*Flower shape.*—Sterile and fertile flowers; rotate.

*Flower buds.*—Sterile flowers; an average of 7 mm in length and 6.5 mm in diameter, obovate in shape, color; 145B suffused with 185A at the apex and margins, fertile flowers; an average of 3 mm in length and diameter, broadly obovate in shape, color; 145C suffused with 58C to 58D at the apex and 144B at the base.

*Peduncles.*—An average of 10 cm in length and 8 mm in diameter, held upright to outwards, 144A in color, smooth surface, strong.

*Pedicels.*—Sterile flowers; an average of 2.4 cm in length and 1 mm in diameter, held at an average angle of 40° to peduncle, 70C in color, moderate strength, dull surface is moderately covered with thin hairs; an average of 0.2 mm in length and NN155A in color, fertile flowers; an average of 3 mm in length and 1 mm in diameter, held at an average angle of 15° to vertical, 151B in color, moderate strength, dull and glabrous surface.

*Petals.*—Sterile flowers; about 4 to 5, rotate, ovate in shape, concave, acute apex, cuneate base, entire margin, an average of 2.8 mm in length and 2 mm in width, glabrous and dull upper and lower surfaces, color when opening and when fully opened; upper surface 69B and lower surface 70D, color does not fade, petals drop when mature, fertile flowers; an average of 5, rotate, ovate in shape, concave, acute apex, cuneate base, entire margin, an average of 2.5 mm in length and 1.75 mm in width, color; upper surface N155B and lower surface 69D with apex 68B, petals drop as maturing, both surfaces glabrous and dull.

*Sepals*.—Sterile flowers; an average of 5, rotate in arrangement, broadly rhomboidal to obovate in shape, apex; broadly acute to rounded and occasionally retuse, cuneate base, margin; entire to slightly irregularly dentate to serrate, an average of 2.3 cm in length and 2.5 cm in width, color; upper and lower surfaces when opening a blend between 150C and 157D fading to 58B towards the margins with picotee margins 58A, upper surface is occasionally suffused with 144A to 144C, upper surface when fully open 68B suffused with N155B fading to 58B towards the margin with picotee margins 58A, lower surface when fully open 68C to 68D fading to a blend between 58B and 59D towards the margin 186B, both surfaces; glabrous and dull, fertile flowers; an average of 5, rotate in arrangement, ovate to deltoid in shape, acute apex, broadly cuneate base, entire margin, an average of 1 mm in length and width, color; upper surface when opening and when fully open 145B, lower surface when opening and when fully open 145B fading to 146B towards the apex, colors do not fade, both surfaces glabrous and dull.

Reproductive organs:

*Gynoecium*.—Sterile flowers; 2 pistils, an average of 1.75 mm in length, stigma; club-shaped and 157D in color, style; 1 mm in length, 145B to 145C in color, ovary is 145A in color, fertile flowers; an average of 3 pistils; an average of 1.75 mm in length, stigma; club-shaped and 157D in color, style; 1.25 mm in length, 145C in color, ovary is 145B to 145C in color.

*Androecium*.—Sterile flowers; an average of 10 stamens, filaments; an average of 1.2 mm in length and 155A in color, anthers; oblong in shape, an average of 0.5 mm in length and 155A in color, pollen not detected, fertile flowers; an average of 10 stamens, filaments; an average of 1 mm in length and 150D in color, anthers; irregular broad reniform in shape, an average of 0.5 mm in length and 157D in color, pollen not detected.

*Fruit and seed*.—No seeds or fruit observed to date.

It is claimed:

1. A new and distinct cultivar of *Hydrangea* plant named 'Horthamp' substantially as herein illustrated and described.

* * * * *